(12) United States Patent
Sambelashvili et al.

(10) Patent No.: US 7,941,218 B2
(45) Date of Patent: May 10, 2011

(54) APPARATUS AND METHODS OF OPTIMIZING ATRIOVENTRICULAR PACING DELAY INTERVALS

(75) Inventors: Aleksandre T Sambelashvili, Maple Grove, MN (US); Thomas J Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 506 days.

(21) Appl. No.: 12/047,876

(22) Filed: Mar. 13, 2008

(65) Prior Publication Data

US 2009/0234411 A1 Sep. 17, 2009

(51) Int. Cl.
*A61N 1/365* (2006.01)
(52) U.S. Cl. ........................................................ 607/17
(58) Field of Classification Search .............. 607/9–11, 607/17–18, 25–26
See application file for complete search history.

(56) References Cited

U.S. PATENT DOCUMENTS

| | | | |
|---|---|---|---|
| 5,179,949 A | 1/1993 | Chirife | |
| 5,741,308 A | 4/1998 | Sholder | |
| 6,876,881 B2 | 4/2005 | Baumann et al. | |
| 7,079,895 B2 | 7/2006 | Verbeek et al. | |
| 7,254,442 B2 | 8/2007 | Van Gelder et al. | |
| 7,702,390 B1 * | 4/2010 | Min | 607/9 |
| 2004/0193223 A1 | 9/2004 | Kramer et al. | |
| 2004/0230243 A1 | 11/2004 | Haefner et al. | |
| 2005/0131480 A1 | 6/2005 | Kramer et al. | |
| 2005/0209648 A1 | 9/2005 | Burnes et al. | |
| 2007/0208386 A1 | 9/2007 | Kramer et al. | |

FOREIGN PATENT DOCUMENTS

EP 1 629 863 3/2006

OTHER PUBLICATIONS

PCT International Search report, PCT/US09/036027, 3 pages.
Raul Chirife, M.D., et al., "Prediction of Interatrial and Interventricular Electromechanical delays from P/QRS Measurements: Value for Pacemaker Timing Optimization", Feb. 2008, *Pacing and Clinical Electrophysiology: PACE*, vol. 31, No. 2, pp. 177-183.

* cited by examiner

*Primary Examiner* — Carl H Layno
*Assistant Examiner* — Jessica Sarcione
(74) *Attorney, Agent, or Firm* — Stephen W. Bauer; Reed A. Duthler

(57) ABSTRACT

Methods and apparatus for optimizing an atrioventricular (AV) pacing delay interval based upon ECG-based optimization is calculated as a linear function of P-wave duration, sensed PR (intrinsic) interval, sensed or paced QRS duration and heart rate. Since the relationship among these parameters is linear, once the coefficients are solved (which can be any value, including null) with reference to a known optimized AV interval (AVopt) such as from an echocardiographic study, an AVopt value can be dynamically adjusted in an ambulatory subject. The various combinations of values can be loaded into a look up table or calculated automatically. And, since some of the parameters do not typically change much over time they can be determined acutely and fed into the equation while the other values can be measured frequently. The parameter values can be measured by an implantable medical device such as a dual- or triple-chamber pacemaker.

22 Claims, 14 Drawing Sheets

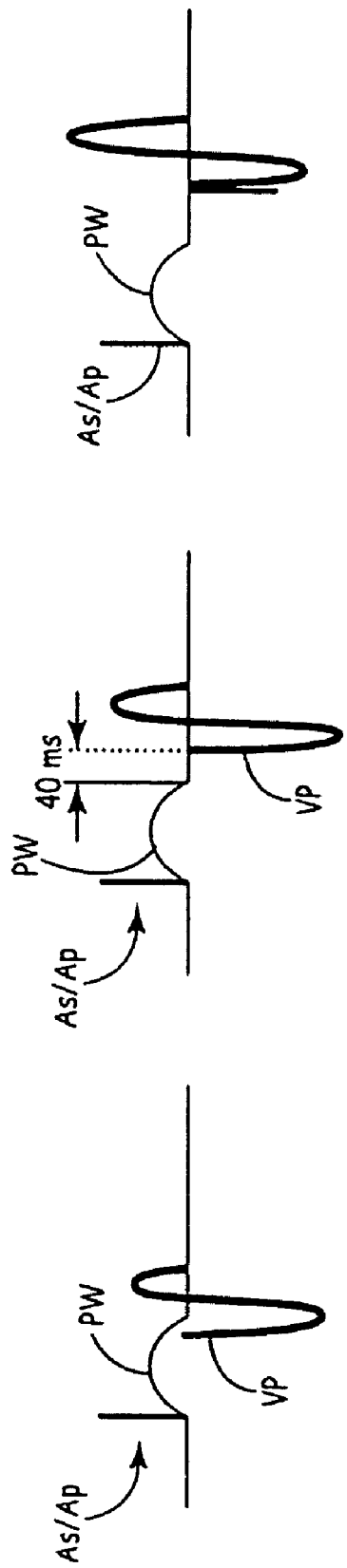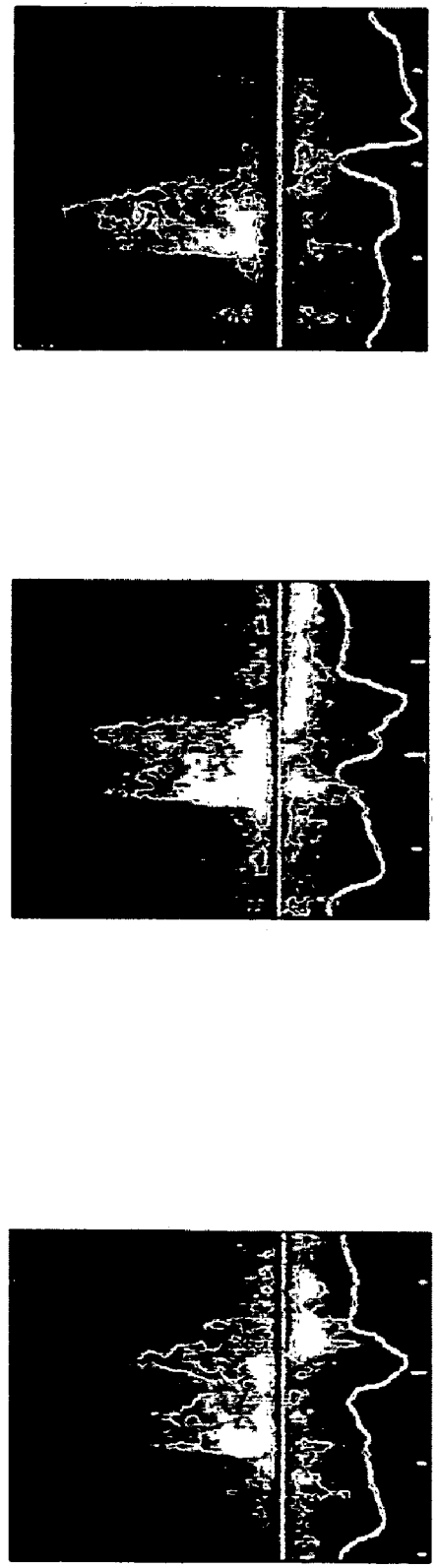
FIG. 7A  FIG. 7B  FIG. 7C

LECG signal processing

1. Filter the signal 0.6 - 16 Hz

2. Calculate rectified derivative

3. Threshold the derivative

APPARATUS AND METHODS OF OPTIMIZING ATRIOVENTRICULAR PACING DELAY INTERVALS

FIELD

This invention relates to cardiac pacing systems, and more particularly to apparatus and methods for improving cardiac function by optimizing atrioventricular (AV) timing intervals for a cardiac pacing system, such as a dual-chamber or a triple-chamber cardiac resynchronization therapy (CRT) delivery system.

BACKGROUND

Cardiac resynchronization therapy (CRT) is a promising and accepted device therapy for patients with systolic heart failure classified in New York Heart Association (NYHA) class III and IV. Indications include patients who, despite optimal medication, are symptomatic, and who demonstrate LV asynchrony. The latter occurs in patients with left bundle branch block (LBBB) and typically presents with a QRS width (measured on an ECG machine) of greater than about 130-150 ms. Herein, "asynchrony" is characterized by a delay in systolic contraction between the intraventricular septum and the left ventricular (LV) free wall.

Currently available CRT bi-ventricular pacing generally employs one lead positioned in operative communication with the right ventricle (RV) and one lead in operative communication with a portion of one of the tributaries of the coronary venous system. The myocardial venous system provides a pathway for deployment of LV stimulation of the lead (and associated electrodes) to operatively communicate with the LV. In most patients, an additional lead is deployed to the right atrium (RA) for atrioventricular (AV) synchronization during pacing. Exceptions for placement of the atrial lead include patients suffering from chronic atrial fibrillation (AF) or having a relatively high AF "burden." According to such CRT delivery, electrical stimulation of both the RV and LV operates to assist ventricular asynchrony and increase contractility (as measured by ventricular pressure development (dP/dt).

CRT has been established as an effective treatment for heart failure patients (NYHA III, IV) with long QRS duration (QRSd>120 ms) and low ejection fraction (EF<35%). A number of acute studies demonstrated a significant dependence of various indices of cardiac function on the programmed values of the atrio-ventricular (AV) and inter-ventricular (VV) delays. The most commonly used methods of AV and VV delay interval optimization are based on echocardiographic evaluation of filling characteristics, cardiac output (CO), and ventricular dyssynchrony for different interval settings. A few chronic studies demonstrated limited evidence of long-term benefit of echo-guided interval optimization. However, considering supposedly incremental benefit of interval optimization such methods seem to be too time and resource-consuming. For certain patients, further optimization of the AV interval can be performed on the guidance of echocardiographic or hemodynamic parameters as is known in the art. However, such methods of optimization of the programmed AV delays in triple chamber (e.g., CRT delivery) implantable medical devices (IMDs) involve complexities. With supposedly incremental benefit of optimization, echocardiographic evaluation simply takes too much time and effort for clinicians (and clinics) and requires coordination between implanting physicians and imaging personnel and equipment. Besides the time, effort and coordination required, the patient is typically lying down and essentially stationary during the procedure. Accordingly, the patient's hemodynamic state during optimization simply does not correlate to the state during activities of daily living (ADL); this is, when the patient is ambulatory.

Thus, there is a need in the art for an improved, easily optimized pacing therapy delivery system that does not need take the above-noted factors into consideration while preserving the benefits of the pacing system described above. Specifically, there is a need for apparatus and methods to easily and efficiently optimize AV intervals to beneficially support and appropriately control pacing therapy and CRT delivery.

SUMMARY

Embodiments of the invention provide relatively simple apparatus and methods of AV timing optimization based on intracardiac electrograms, subcutaneous, or surface ECG. Such apparatus and methods are highly desirable as a simple and effective means of assuring optimized pacing delivery. Certain embodiments provide complex echocardiographic interval optimization by being based on surface, subcutaneous (so-called leadless arrays providing electrode vectors) ECG and/or intracardiac EGM signals and can be performed acutely and chronically.

In one embodiment, assuming a patient has normal atrial rhythm, the AV interval is programmed in such a way that the time interval between the end of the P-wave (PWend) and the beginning of the QRS complex (QRSbeg or Q-wave) is close to or no less than a certain fixed value (e.g. between about 30 ms and 60 ms, or a nominal value of about 40 ms). In one form of this embodiment, either the duration of the P-wave or the termination of the P-wave is evaluated manually. A clinician could electronically measure this using surface ECG on a display or use a caliper on a printed temporal strip of cardiac cycles. In another form of the this embodiment, the termination (PWend) or duration of the P-wave (PWd) is determined automatically with an novel algorithm. The algorithm begins operating when an atrial event is sensed (intrinsic or paced), which can be a far-field signal sensed from electrodes spaced from the heart or near field electrodes within or about the heart. The sensed signal is then filtered and the time derivative of the P-wave (dPW/dt) is taken and rectified resulting in a waveform having, for example, two peaks. In this case either of the rectified peaks can be used as a reference as the algorithm proceeds. A nominal threshold is set based at least in part on the peak signals (P1, P2, P3, etc), such as about 15% or about 30% (or other effective value) of the amplitude thereof, and a temporal window having a nominal length (e.g., 5, 8, 10, 12 ms) is translated from one of the peaks. When the rectified signal within the temporal window is completely below the threshold, the end of PWend is declared and optionally, PWd can be calculated (beginning with a sensed atrial event, As, or a paced atrial event Ap). In a related aspect, PWd alone provides an indication of a subject's susceptibility to atrial arrhythmias such as atrial flutter and atrial fibrillation (collectively AF). In this aspect, an acute lengthening of the PWd as well as a chronic lengthening, or a trend of increasing PWd values is used as a diagnostic for a subject and his or her attending clinic and clinicians. Inversely, an acute shortening or a trend of increasing shorter PWd values can indicate that a palliative or curative therapy regime is having a positive effect upon the subject or the subject is otherwise possibly improving their cardiac condition or stability.

Of course, the algorithm is not the exclusive manner of determining PWend and PWd, however, as other methods could be utilized such as by determining changes to the slope of the P-wave signal, threshold crossings, changing polarity of the signal, and the like.

In one embodiment, the AV delay based on ECG-based optimization is calculated as a linear function of baseline P-wave duration (PWd), baseline PR (intrinsic) interval, baseline or paced QRS duration (QRSd) and heart rate (HR), as follows:

$$AVopt=a*PWd+b*QRSd+c*PR+d*HR+f$$

Since this is a linear equation the coefficients a, b, c, d, and f can be determined from the best fit to the AVopt determined using other conventional approaches, such as echocardiography or the like. Thereafter, either a look up table (LUT) or the equation itself can be used to dynamically adjust the AVopt values over a wide range of conditions. In another aspect, since some of the values change relatively little over most of the physiologic conditions experienced by patients receiving CRT, they can essentially be determined and set. This applied, for example, to the P-wave duration (PWd) and the QRS duration (QRSd) thereby requiring essentially only two measurements; namely, PR interval (from an As event to a ventricular sense Vs event) and heart rate (HR) as a reasonable approximation for deriving an AVopt value that will maximize (left) ventricular filling in an ambulatory heart failure patient.

Cardiac activity may be sensed with a far-field sensing system; such as a shroud or surround-type subcutaneous electrode array (SEA), such as that disclosed and depicted in co-pending application Ser. No. 11/687,465 filed 16 Mar. 2007, the contents of which are incorporated herein by reference. The inventors note that so-called far field electrode vectors, such as via a SEA or a coil-to-can vector, often produce less noise than near field (e.g., tip-to-ring) vectors although a variety of different vectors can be tested and compared for the one that best senses P-waves. Of course, any temporary or chronically implantable medical electrical lead can be used to sense cardiac activity (e.g., intracardiac, transvenous, and/or epicardial electrodes) deployed about the heart and used to define appropriate sensing vectors to capture the signals (esp. P-waves) from the cardiac activity. As noted above, surface electrodes coupled to a display or to an IMD programming device can also be used. Such electrodes can be coupled to a medical device programmer or ECG machine each optionally having hard print capability and/or a display. Currently available programming devices and ECG equipment can be utilized. Although exemplary programmers, among others, include U.S. Pat. No. 7,209,790 entitled Multimode Programmer for Medical Device Communication and U.S. Pat. No. 6,931,279 entitled Method and Apparatus for Implementing Task-oriented Induction Capabilities in an Implantable Cardioverter Defibrillator and Programmer, the contents of which are incorporated herein by reference.

The foregoing and other aspects and features will be more readily understood from the following detailed description of the embodiments thereof, when considered in conjunction with the drawings, in which like reference numerals indicate similar structures throughout the several views.

BRIEF DESCRIPTION OF THE DRAWINGS

FIGS. 7A-C are paired depictions of a (too) short AV interval, a recommended AV interval, and a (too) long AV interval wherein the lower is a doppler echocardiographic image of mitral flow resulting from the different AV intervals.

DETAILED DESCRIPTION OF THE ILLUSTRATED EMBODIMENTS

A Methods and apparatus are provided to optimize timing intervals for and/or monitor a subject receiving pacing therapy, including cardiac resynchronization therapy (CRT) to improve the hemodynamics of the subject to closely mimic a normal depolarization-repolarization cardiac cycle sequence.

Figure 1:
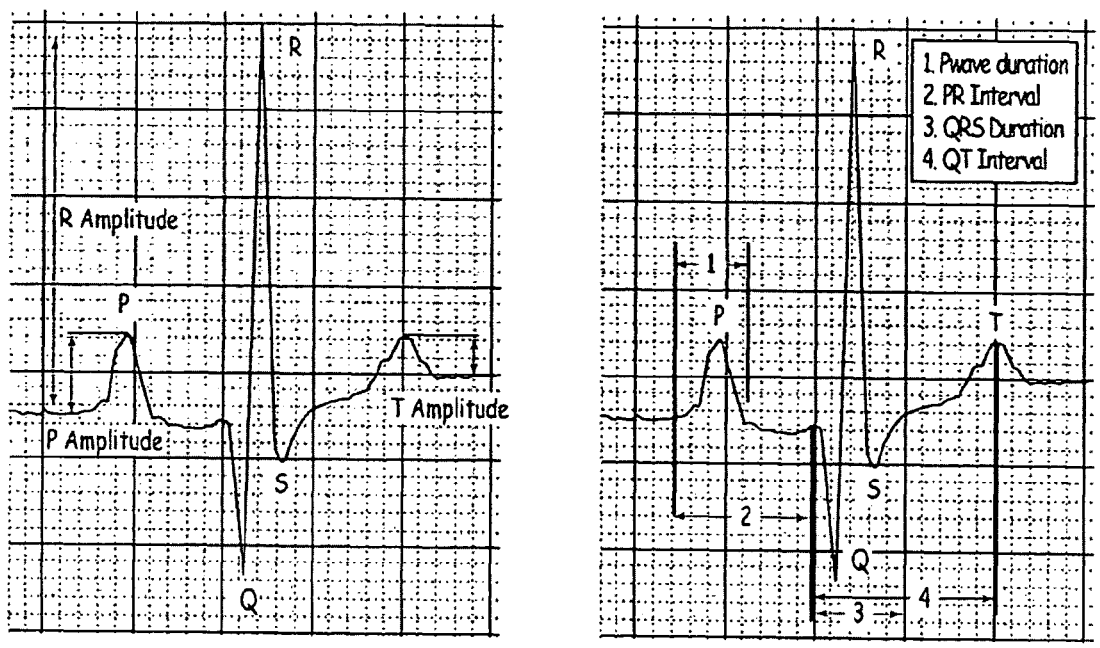
FIG. 1 is a pair of illustrations of a cardiac depolarization and repolarization waveforms with the PQRST complex indicated by a corresponding letter and the P-wave duration (herein PWd), PR interval, QRS duration (QRSd) and QT interval of a normal intrinsic electrical activation sequence.

FIG. 1 is a pair of illustrations of a cardiac depolarization and repolarization waveforms with the PQRST complex indicated by a corresponding letter and the P-wave duration (herein PWd) indicated at reference numeral 1, PR interval 2, QRS duration (QRSd) 3 and QT interval 4 of a normal intrinsic electrical activation sequence.

Figure 2:
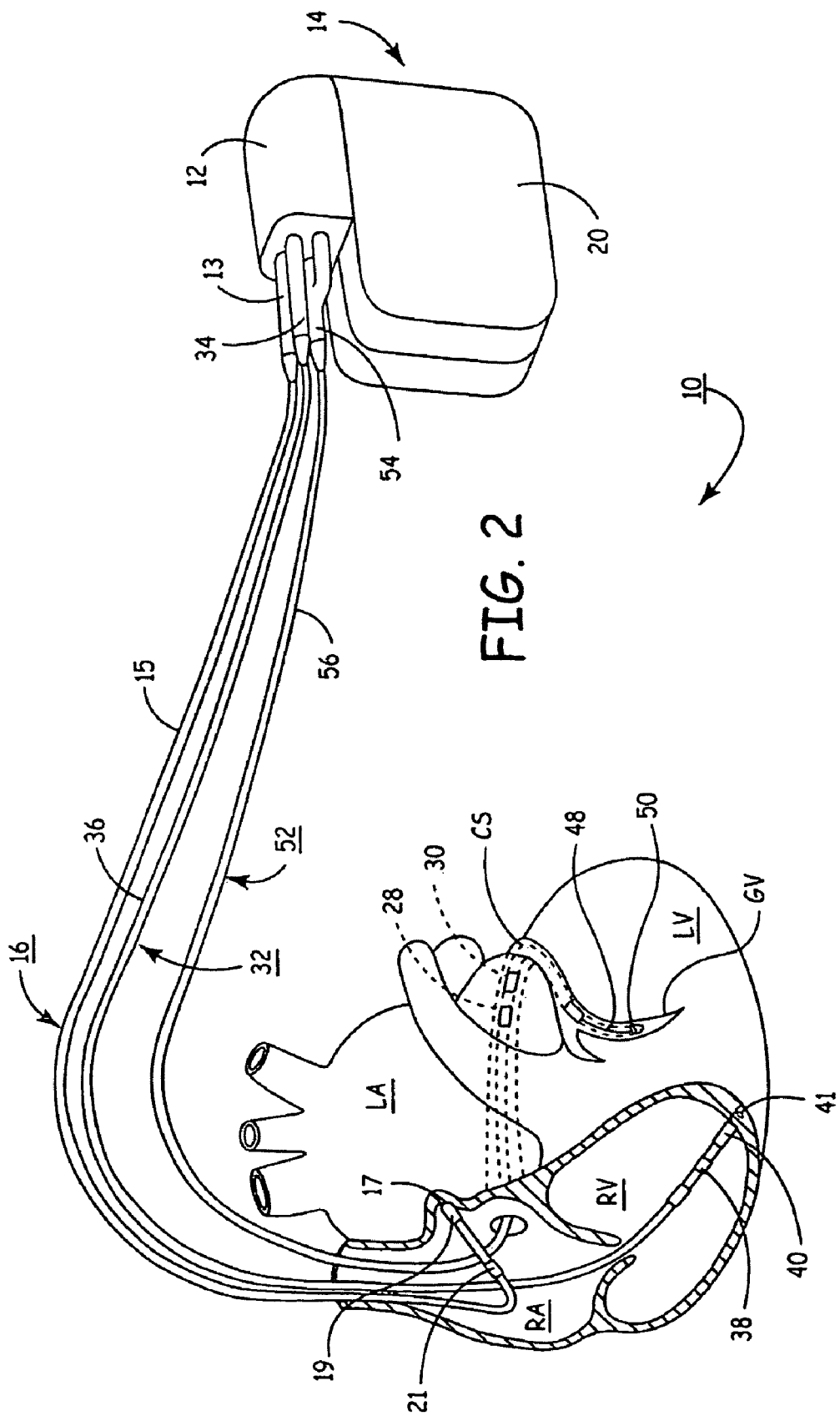
FIG. 2 is a schematic diagram depicting a three channel, atrial and bi-ventricular, pacing system.

FIG. 2 is a schematic representation of an implanted, triple-chamber cardiac pacemaker comprising a pacemaker IPG 14 and associated leads 16, 32 and 52. The pacemaker IPG 14 is implanted subcutaneously in a patient's body between the skin and the ribs. The three endocardial leads 16,32,52 operatively couple the IPG 14 with the RA, the RV and the LV, respectively. Each lead includes at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. In addition, mechanical and/or metabolic sensors can be deployed independent of, or in tandem with, one or more of the depicted leads.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this embodiment, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
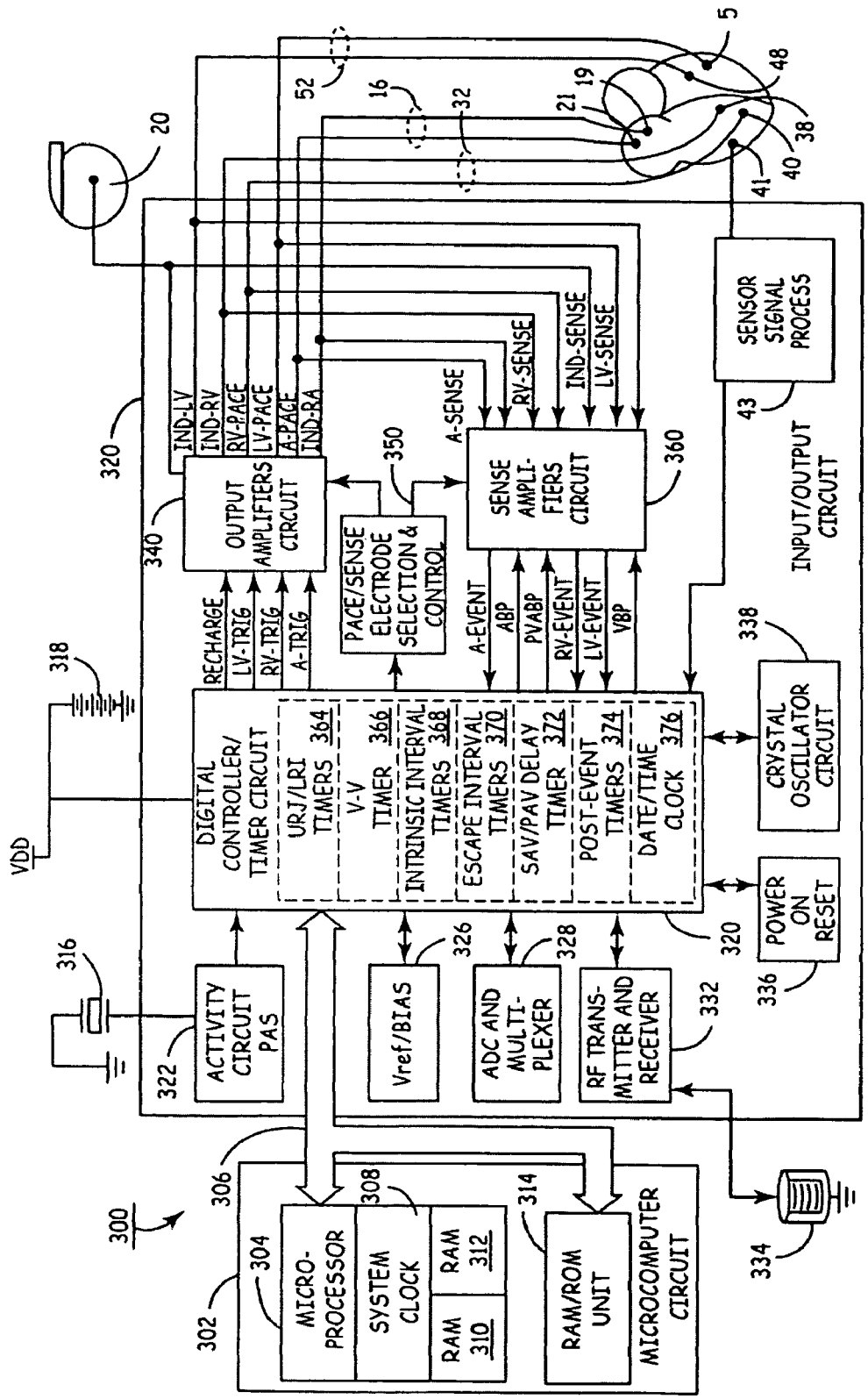
FIG. 3 is a simplified block diagram of one embodiment of IPG circuitry and associated leads employed in the system of FIG. 2 for providing three sensing channels and corresponding pacing channels that functions to provide therapy to and/or monitor a subject.

Further, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. In addition, at least one physiologic sensor 41 is depicted operatively coupled to a portion of myocardium and electrically coupled to a sensor signal processing circuit 43. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, embodiments of this invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, embodiments of the invention may also be practiced in non-rate responsive pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V interval, as applicable. In addition, the microprocessor 304 may also serve to define variable AV delays and the uni-ventricular, pre-excitation pacing delay intervals (A-LVp) from the activity sensor data, metabolic sensor(s) and/or mechanical sensor(s).

In one embodiment, microprocessor 304 is a custom microprocessor adapted to fetch and execute instructions stored in RAM/ROM unit 314 in a conventional manner. It is contemplated, however, that other implementations may be suitable. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to this discussion are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay (or A-RVp delay) from a preceding A-EVENT or A-TRIG, a post-ventricular timer 374 for timing post-ventricular time periods, and a date/time clock 376.

The AV delay interval timer 372 is loaded with an operating AV interval for the ventricular chamber to time-out starting from a preceding atrial event whether paced or intrinsic in nature, herein Ap and As, respectively. In one form, the AV interval is set to a nominal value such as 40 milliseconds as measured from the detected end of the P-wave to the beginning of the QRS complex.

Another embodiment involves adjustment of the time interval between the end of P-wave (PWend) and the end of paced QRS (QRSend) to a fixed predetermined value (e.g. 150 ms). In the most generic embodiment of ECG-based optimization the optimal AV delay is calculated as a linear function of baseline P-wave duration (PWd), baseline PR (intrinsic) interval, baseline or paced QRS duration (QRSd) and heart rate (HR):

$$AVopt = a*PWd + b*QRSd + c*PR + d*HR + f;$$

In addition the inventors discovered that the heart rate (HR) has an effect upon value of an optimal AV delay. If Rate-Adaptive AV (RAAV) feature is programmed on, the minimum AV in the RAAV feature should be programmed to AVopt$-$(PWend$-$to $-$QRSbeg/end$-\epsilon$ms) where $\epsilon$ is a fixed value, such as a nominal 40 ms. RAAV should then be programmed as to decrease the sensed AV (SAV) and paced-AV (PAV) by one ms for every one beat per minute (bpm) increase in the HR.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE that may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE that may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay or the LV-TRIG at the time-out of the A-LVp delay provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As noted in the above-referenced, commonly assigned, '324 patent, a very high impedance P-wave and R-wave sense amplifiers may be used to amplify the voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Operative circuitry 300 of FIG. 3 includes RR interval comparator 301, coupled to RV sensing electrodes coupled to lead 32, LV pacing electrodes coupled to LV pacing electrodes coupled to lead 52. In one embodiment, an AV interval adaptation circuit 305 operates to adjust and maintain the AV delay interval at an optimized value. The AV interval adaptation circuit 305 may include circuitry for modifying the optimum AV interval value in the case a rate-adaptive AV feature is programmed "on" such that the interval will decrease approximately one millisecond (ms) for each one bpm a subject's heart rate increases. In another aspect, the circuit 305 (in conjunction with memory structures) includes tracking capability so that as, for instance, the end of the P-wave (PWend) or the duration of the P-wave (PWd) changes and thus, the AV interval varies, these values can be subsequently reviewed. One of a pair of output signals from the AV interval adaptation circuit 305 operatively connect to atrial sensing and pacing electrodes that are coupled to atrial lead 16. The other of the pair of output signals from the AV interval adaptation circuit 305 operatively connects to LVp electrodes coupled to pacing electrodes coupled to the lead 52.

As noted hereinabove, a subcutaneous electrode array (SEA) can be used to sense P-waves from a location spaced from the heart. On such SEA that can be coupled to or incorporated into an subcutaneously implanted device is shown in FIG. 4 which is an elevational side view depicting an exemplary shroud assembly coupled to an IMD which illustrates electrical conductors disposed in the header, or connector, portion of the IMD which is configured to receive a proximal end portion of medical electrical leads (not shown).

Figure 4:
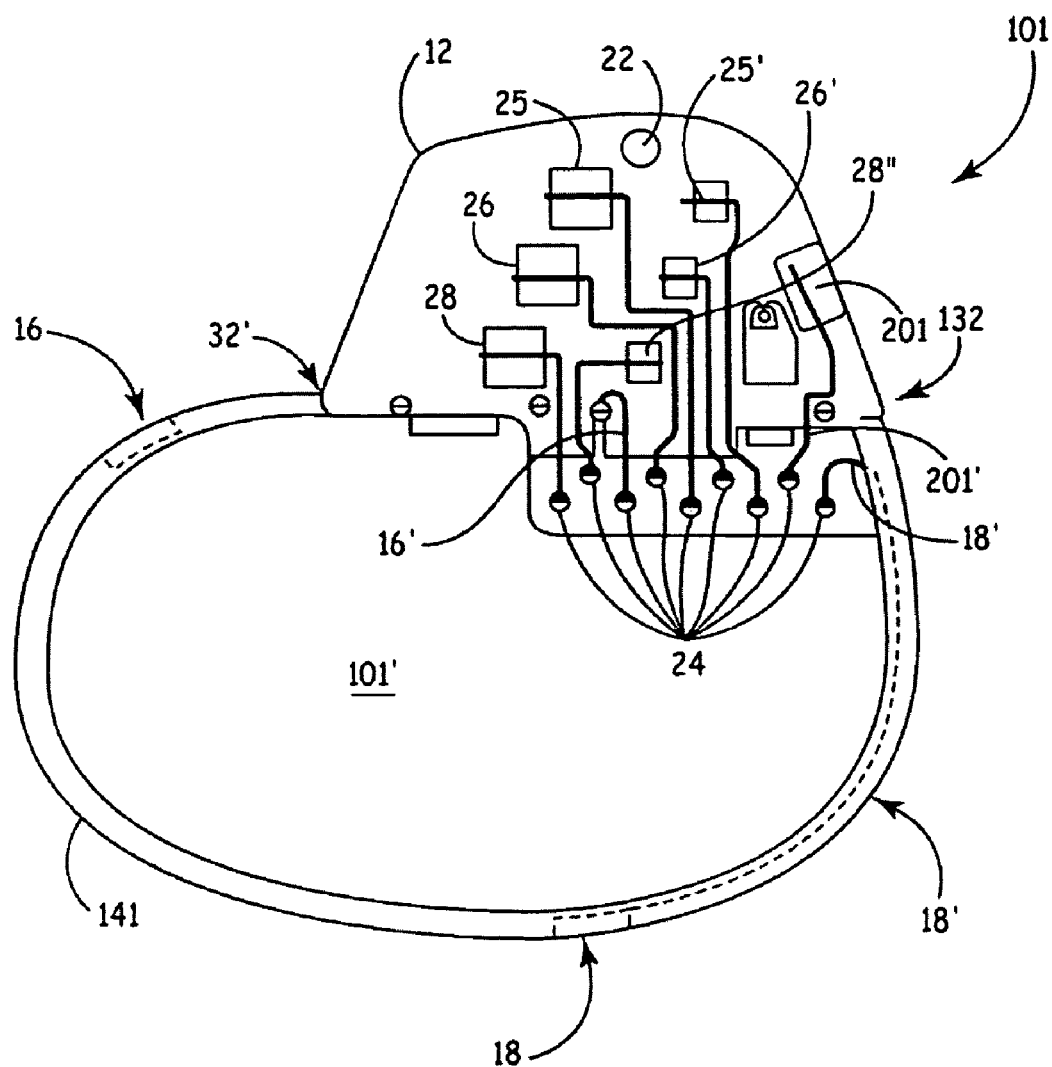
FIG. 4 is an elevational side view depicting an exemplary far-field shroud assembly coupled to an IMD, which illustrates electrical conductors disposed in the header, or connector, portion of the IMD that are configured to couple to end portions of medical electrical leads as well as couple to operative circuitry within the IMD housing.

FIG. 4 depicts an exemplary shroud assembly 141 coupled to an IMD 101 which illustrates electrical conductors 25,26, 28' disposed in the header, or connector, portion 12 of the IMD 10 which are configured to couple to end portions of medical electrical leads as well as couple to operative circuitry within the IMD housing (not shown). The shroud assembly 141 surrounds IMD 101 and mechanically couples to the header portion 12 and includes at least three discrete electrodes 16,18,201 adapted for sensing far-field, or extra-cardiac electrogram (EC-EGM) signals. FIG. 4 also depicts an aperture 22 formed within the header 12 which can be used to receive thread used to suture the header 12 (and thus the IMD 101) to a fixed surgical location (also known as a pocket) of a patient's body.

As partially depicted in FIG. 4, an elongated conductor 18' couples to electrode 18, elongated conductor 16' couples to electrode 16, and conductor segment 201' couples to electrode 201. Furthermore, three of the conductors (denoted collectively with reference numeral 24) couple to three cuff-type conductors 25,26,28' adapted to receive proximal portions of medical electrical leads while another three of the conductors couple to conductive pads 25',26',28" which are aligned with, but spaced from the conductors 25,26,28' along a trio of bores (not shown) formed in header 12.

Figure 5:
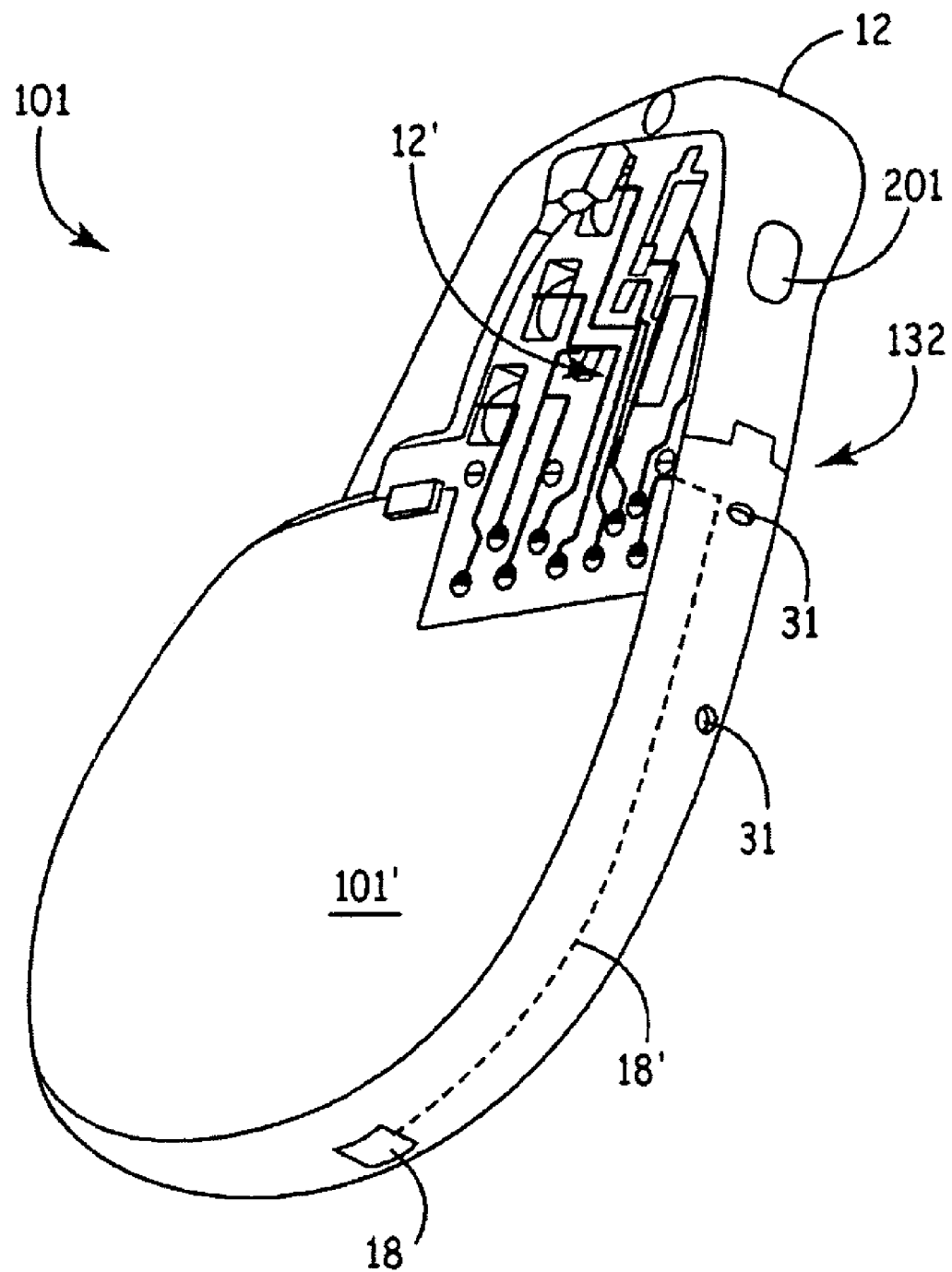
FIG. 5 is a perspective view of the IMD depicted in FIG. 4 further illustrating the shroud assembly and two of the three electrodes.

FIG. 5 is a perspective view of the IMD 101 depicted in FIG. 4 further illustrating the shroud assembly 141 and two of the three electrodes 18,201. In addition, two of a plurality of adhesive ports 31 and a mechanical joint 132 between the elongated portion of the shroud assembly 141 and the header 12 are also depicted in FIG. 5. The ports 31 can be used to evacuate excess medical adhesive disposed between the shroud assembly 14 and the IMD 10 and/or used to inject medical adhesive into one or more of the ports 31 to fill the void(s) therebetween. In one form of the invention, a major lateral portion 12' of header 12 remains open to ambient conditions during assembly of the IMD 101. Subsequent to making electrical connections between the plurality of conductors of the shroud assembly 141 and the header 12, the open lateral portion 12' is sealed (e.g., automatically or manually filled with a biocompatible substance such as a substantially clear medical adhesive, such as Tecothane® made by Noveon, Inc. a wholly owned subsidiary of The Lubrizol Corporation). Thus most if not all of the plurality of conductors of the shroud assembly 141 and the IMD 101 are visible and can be manually and/or automatically inspected to ensure long term operability and highest quality of the completed IMD 101.

Referring again to FIG. 4, the terminal ends of conductors 24 are depicted to include the optional shaped-end portion which provides a target for reliable automatic and/or manual coupling (e.g., laser welding, soldering, and the like) of the terminal end portions to respective conductive pins of a multi-polar feedthrough assembly (not shown). As is known in the art, such conductive pins hermetically couple to operative circuitry disposed within the IMD 101.

Figure 6:
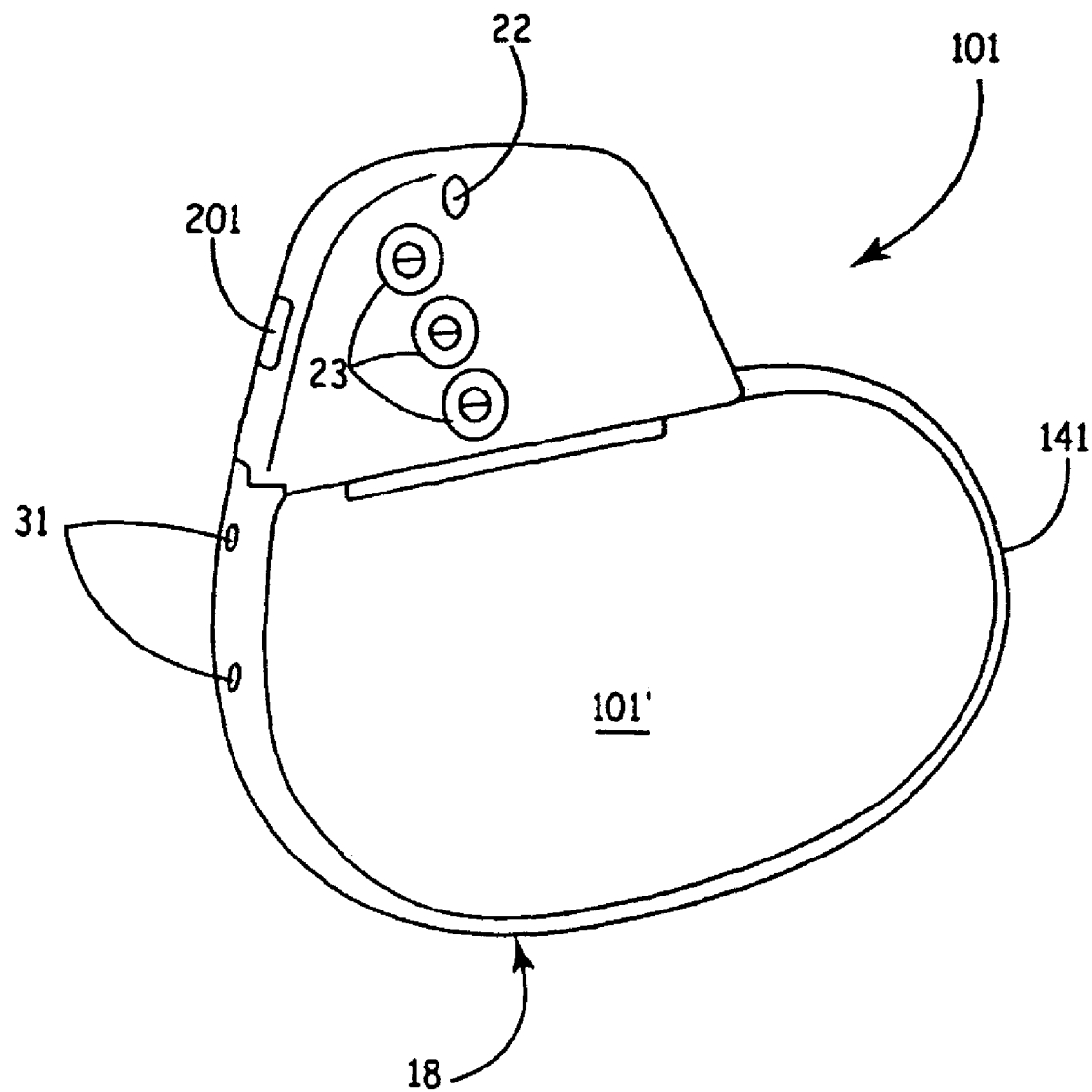
FIG. 6 is a perspective view of an opposing major side 10" of the IMD 10 depicted in FIGS. 4 and 5 and three self-healing grommets 21 substantially hermetically coupled to openings of a like number of threaded bores.

FIG. 6 is a perspective view of an opposing major side 101' of the IMD 101 depicted in FIGS. 4 and 5 and three self-healing grommets 23 substantially hermetically coupled to openings of a like number of threaded bores (not shown). As is known, the threaded bores are configured to receive a threaded shank and the grommets 23 are fabricated to temporarily admit a mechanical tool (not shown). The tool is used to connect and allow a physician or clinician to manually tighten the conductors 25,26,28', for example, with compression and/or radially around conductive rings disposed on proximal portions of medical electrical leads (not shown). In addition, two of the plurality of ports 31 are also depicted in FIG. 6.

FIGS. 7A-C are paired depictions of a (too) short AV interval, a recommended AV interval, and a (too) long AV interval wherein the lower is a doppler echocardiographic image of mitral flow resulting from the different AV intervals. In FIG. 7A, the ventricular pacing stimulus Vp impinges up the P-wave (PW) thereby not allowing adequate atrial "kick" nor complete ventricular filling. In FIG. 7B, a nominal 40 ms time interval is maintained following the end of the P-wave (PWend), which can be located per the algorithm detailed at FIG. 10 hereinbelow. FIG. 7C depicts an AV interval that is too long and wherein the mitral flow is inhibited due to the lack of coordination of atrial and ventricular function.

Figures 8A, 8B, 8C:
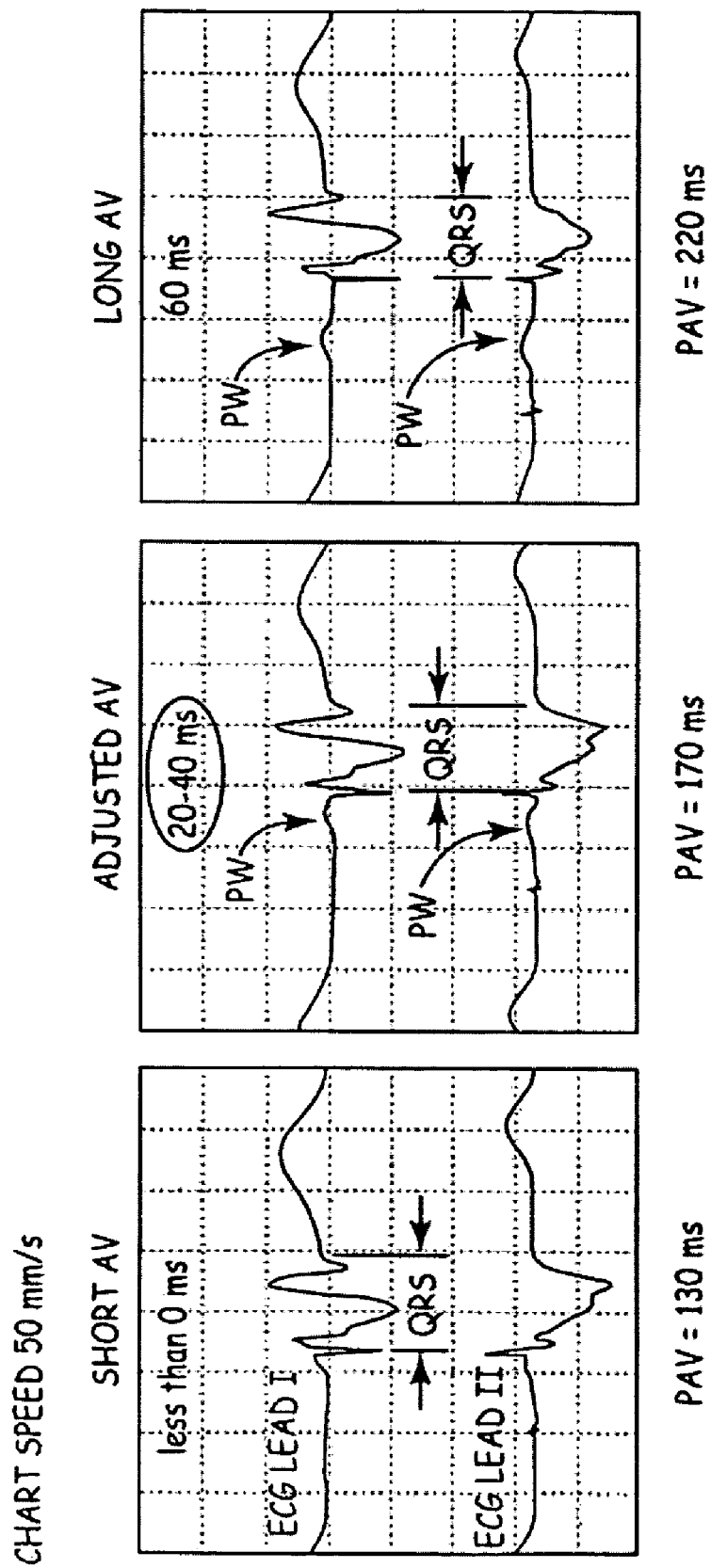
FIGS. 8A-C depict signals from a pair of surface electrodes (lead I and II) wherein a paced-AV (PAV) interval varies from 130 ms ("short AV"), to 170 ms (adjusted AV), to 220 ms (long AV) showing how the relative location of the P-wave and the beginning of the QRS complex changes with differing PAV interval.

FIGS. 8A-C depict signals from a pair of surface electrodes (lead I and II) wherein a paced-AV (PAV) interval varies from 130 ms ("short AV"), to 170 ms (adjusted AV), to 220 ms ("long AV") showing how the relative location of the P-wave (PW) and the beginning of the QRS complex (QRS) changes with differing PAV interval. In FIG. 8A, it is apparent that when the PAV is set to 130 ms the PW is truncated and as depicted the trace from the lead labeled ECG Lead I literally collides with the QRS complex and related fluid and electro-mechanical activity. Also, in FIG. 8A the ECG Lead II did not even pick up the PW from that particular cardiac cycle. In FIG. 8B, at a PAV of 170 ms the PW ends approximately 20-40 ms before the beginning of the QRS complex and as noted in FIGS. 7A-C the concomitant ventricular filling is maximized. In FIG. 8C at a PAV of 220 ms, approximately 60 ms elapses after the end of the P-Wave but before the QRS complex commences.

Figure 9C:
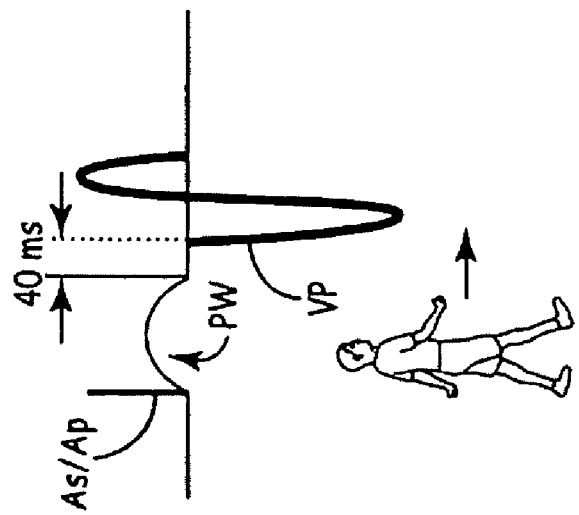
FIGS. 9A-C are paired images illustrating an embodiment wherein an optimized AV interval, AVopt, is shortened during increased heart rate excursion and then returned to the AVopt interval following the increased heart rate excursion.
Figure 9B:
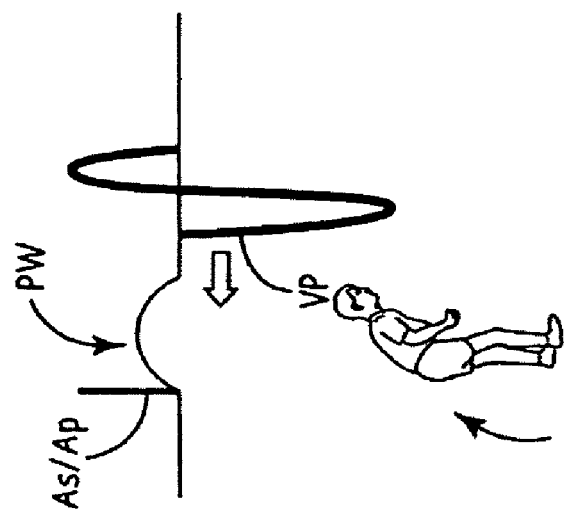
Figure 9A:
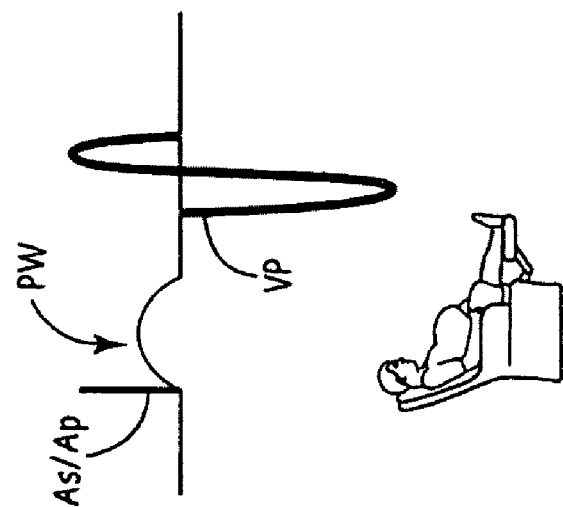

FIGS. 9A-C are paired images illustrating an embodiment wherein an optimized AV interval, AVopt, is shortened during increased heart rate excursion and then returned to the AVopt interval following the increased heart rate excursion. The AVopt interval is shortened to not less than a minimum value defined as AVopt less the interval between the end of the P-wave and either the beginning or end of the QRS complex (and less a nominal additional amount, such as about 40 ms). When the patient's heart rate stabilizes then the AVopt interval can resume operation (or an adapted value can be utilized according to certain of the embodiments described hereinbelow.

Figure 10A:
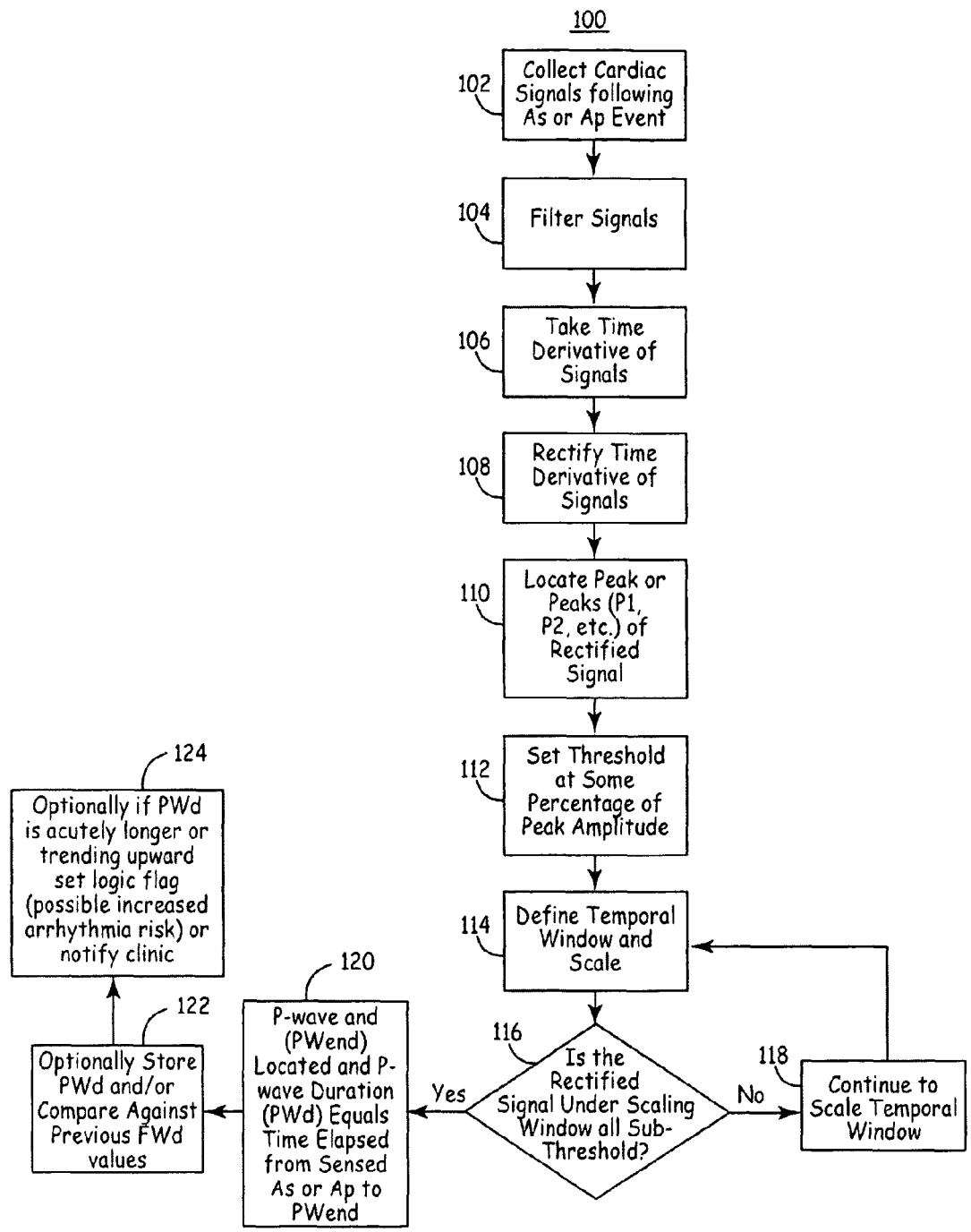
FIG. 10A is a flow chart illustrating an embodiment for measuring the end of a P-wave (PWend) and/or the duration of a P-wave (PWd) and FIG. 10B is a depiction of a portion of the process depicted in FIG. 10A.
Figure 10B:
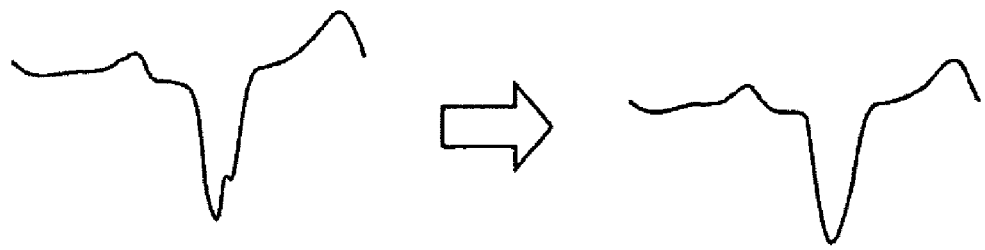
Figure 10B:
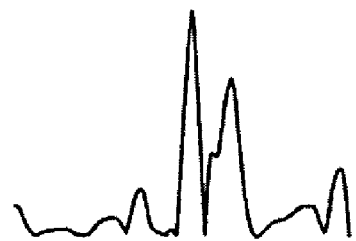
Figure 10B:
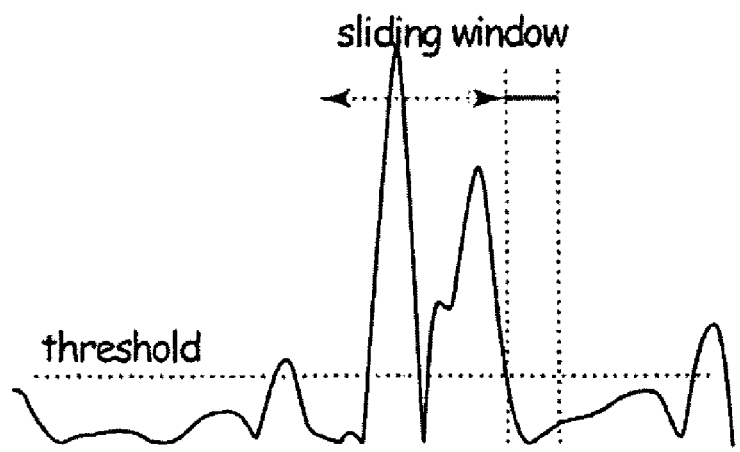

FIG. 10A is a flow chart illustrating an embodiment for measuring the end of a P-wave (PWend) and/or the duration of a P-wave (PWd). FIG. 10A can be reviewed along with the simplified illustration of FIG. 10B, which provides a depiction of a waveform being processed according to method 100. Now The method 100 begins at 102 with collection of cardiac signals following either a sensed or paced atrial event (As or Ap). The sensed signals are then filtered at 104 and the time derivative (dPW/dt) is taken at 106. The resulting waveform is of course sinusoidal as the P-wave is a generally smoothly rising and then falling signal. At step 108 the derived sinusoidal P-wave is rectified thus resulting in a dual-humped signal. A peak of this signal is located at step 110 from either peak (P1 or P2) and a threshold is set based at least in part upon the amplitude of either peak P1 or P2 at step 112. The threshold can be a nominal value but a value of about ten to thirty percent (10%-30%) of the peak amplitude of P1 or P2 will suffice. At step 114 a temporal window is scaled from either of the peaks (P1 or P2) until the values of the signal beneath the window are all sub-threshold (116). At that point the end of the P-wave (PWend) has been located and the duration of the P-wave (PWd) can be calculated (at 120) as the time elapsed from the atrial event (As or Ap) until PWend was located. Then optionally, according to certain embodiments, the value of PWd can be stored and/or compared to prior PWd values, thereby providing clinical benefit to a subject as an indicator of cardiac status and/or condition. In addition, the duration of the QRS complex (QRSd) can be measured and compared to prior values. Thus, a notification, alert or notation that the subject is either benefiting or declining status can be performed as will be described hereinbelow.

Figure 11:
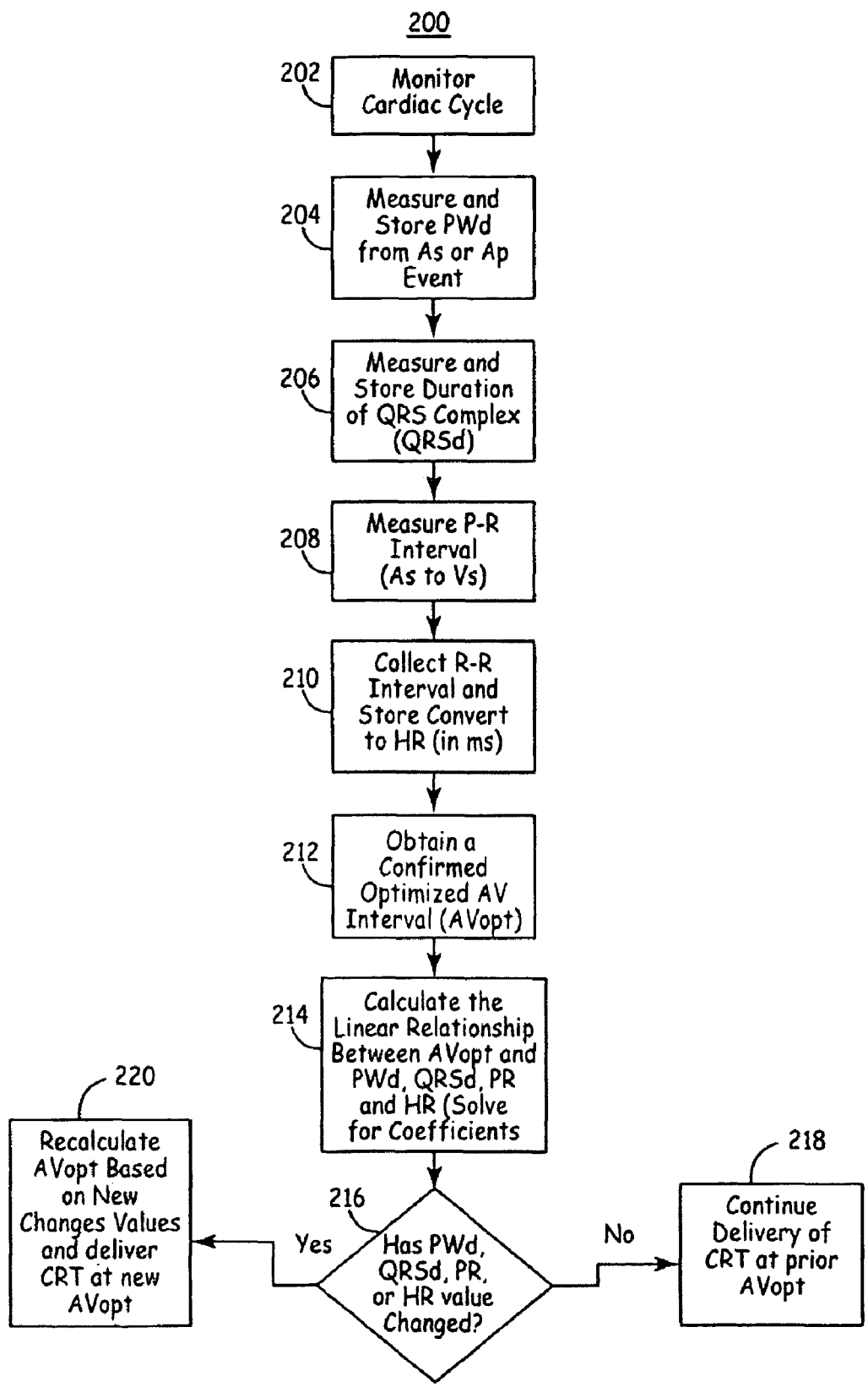
FIG. 11 is a flow chart illustrating a method of calculating the linear relationship between an optimal atrioventricular interval (AVopt) and PWd, QRS complex duration (QRSd), intrinsic P-R interval (PR), and heart rate (HR) so that chronic, dynamic control of the AVopt interval can be realized via the linear relationship or via a look up table (LUT).

FIG. 11 is a flow chart illustrating a method 200 of calculating the linear relationship between an optimal atrioventricular interval (AVopt) and PWd, QRS complex duration (QRSd), intrinsic P-R interval (PR), and heart rate (HR) so that chronic, dynamic control of the AVopt interval can be realized via the linear relationship or via a look up table (LUT). The cardiac cycle of subject is monitored at 202 and the P-wave duration (PWd) is measured and stored at 204 as previously described. The duration of the QRS complex of the subject is measured and stored at step 206. The intrinsic P-R interval of the subject is measured as the time between an intrinsic atrial event (As) and a resulting intrinsic ventricular event (Vs) and stored at 208. The heart rate (HR) is then measured as the time between successive QRS complexes (R-R interval) and stored. Then at 212 a confirmed optimized AV interval (AVopt) is obtained, for example using convention echocardiography or other method. Then at 214 the linear relationship is calculated that relates AVopt to PWd, QRSd, PR, and HR (including coefficients). This thus provides a method to dynamically recalculate the AVopt interval based on detected changes to one or more of the four values. That is, the AVopt interval equation can be recalculated or a look up table (LUT) populated with values that correlate the four values. In a related embodiment, the LUT can be simplified somewhat due to the fact that QRSd and PWd change little, if any, over a fairly large ranges of heart rates for most cardiac patients receiving cardiac resynchronization therapy (CRT). So, at step 216, in the event that one or more of the values change the AVopt can be modified at 220. In the event that the values have not changed (or have only changed slightly) at step 218 the CRT delivery continues at the prior value of AVopt preferably using the same gradual rate utilized to previously shorten the AV interval (e.g., one ms per one bpm that the heart rate changes).

Figure 12:
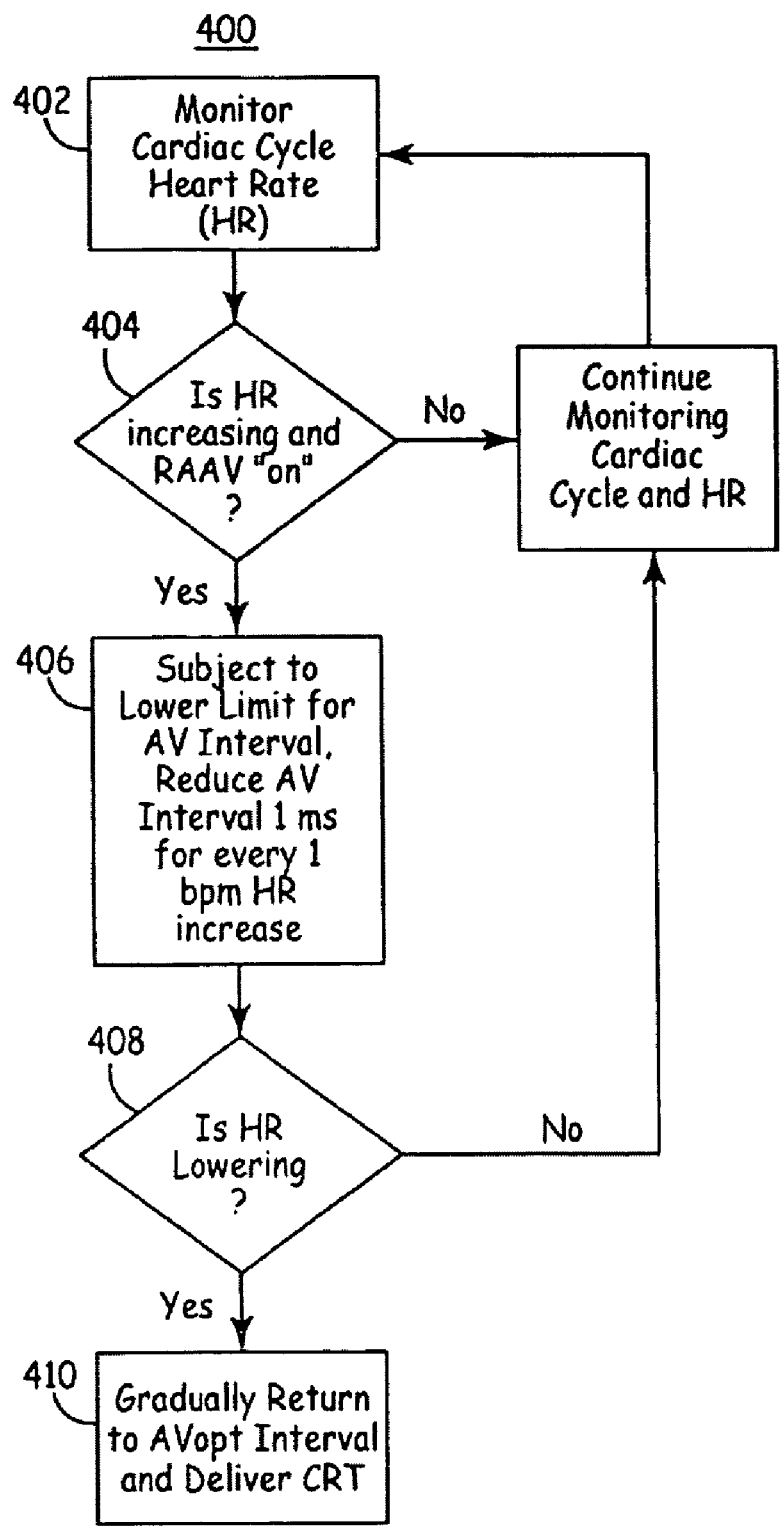
FIG. 12 is a flow chart depicting an embodiment wherein a rate adaptive atrio-ventricular (RAAV) interval is dynamically adjusted during an increasing heart rate excursion, subject to a lower limit for a subject receiving cardiac resynchronization therapy.

FIG. 12 is a flow chart depicting an embodiment 400 wherein a subject receiving cardiac resynchronization therapy and has a rate adaptive atrio-ventricular (RAAV) interval that is dynamically adjusted during an increasing heart rate excursion, subject to a lower limit for a subject receiving cardiac resynchronization therapy. At step 402 the cardiac cycle is monitored and the heart rate metric is calculated. At 404 whether or not the heart rate is increasing or not is determined. If the heart rate is determined not to be increasing then the CRT delivery continues. If, however, the heart rate is determined to be increasing then at 406 the operating AV (AVopt) interval is decreased at a rate of about one millisecond (ms) for every one beat per minute (bpm) the heart rate increases, subject to a limit defined as the AVopt interval less the interval between the end of the P-wave (PWend) and either the beginning or end of the QRS complex (QRSbeg or QRSend) less a nominal value such as 40 ms. In the event that the heart is trending lower then at 410 the value of the operating AV interval is returned to the prior optimized AV interval value (AVopt). If the heart rate is not lowering, then the cardiac cycle continues to be monitored at 402 and process 400 continues.

Figure 13:
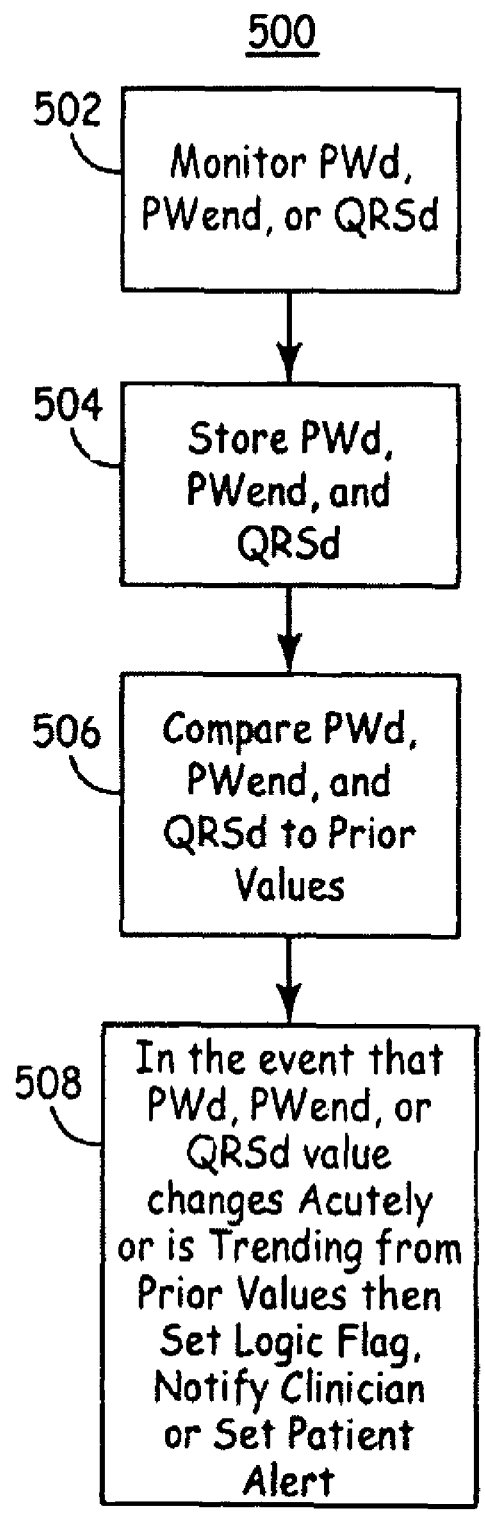
FIG. 13 is a flow chart illustrating a diagnostic and monitoring method for measuring P-wave duration, P-wave endtime, and the duration of the QRS complex (QRSd) to provide notifications, alarm, and/or intervention in the event that one or more of the values acutely or chronically changes from historical values.

FIG. 13 is a flow chart illustrating a diagnostic and monitoring method 500 for measuring the parameters P-wave duration (PWd), P-wave end-time (PWend), and the duration of the QRS complex (QRSd) to provide notifications, alarm, and/or intervention in the event that one or more of the values acutely or chronically changes from historical values. According to this embodiment, the parameters PWd, PWend or QRSd are monitored at step 502 and the values are stored at step 504. The stored values can then be compared at 506 with prior values or evaluated to discern if any trend is occurring in one or more of the parameters. At step 508 any acute changes or trend from prior or historical values is used to trigger a logical flag, provide a notification to a clinic or clinician or the like, store a recent temporal record of recently measured or recorded physiologic events, set a patient alert or the like.

Of course, certain of the above-described structures, functions and operations of the pacing systems of the illustrated embodiments are not necessary to practice the present invention and are included in the description simply for completeness of an exemplary embodiment or embodiments. It will also be understood that there may be other structures, functions and operations ancillary to the typical operation of an implantable pulse generator that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of adjusting an operating atrio-ventricular (AV) interval in a cardiac pacing therapy delivery device, comprising:
   measuring the following temporal cardiac parameters of a subject's heart: a P-wave duration (PWd) value, a sensed intrinsic atrioventrical (PR) interval, a sensed or paced QRS duration (QRSd) value, and a heart rate (HR) for at least one cardiac cycle;
   calculating an optimized AV interval (AVopt) as a linear function of the sensed PWd value, the sensed PR interval value, the sensed or paced QRSd value, and the HR value; and
   storing the calculated AV interval as an operating AV interval in a memory structure of a pacing therapy delivery device.

2. A method according to claim 1, further comprising:
   operating the delivery device in a bi-ventricular pacing mode based at least in part upon the optimized AV interval.

3. A method according to claim 1, further comprising:
   solving a set coefficients for said linear relationship after determining an AVopt interval using a conventional echocardiographic imaging study.

4. A method according to claim 1, wherein the step of measuring the temporal cardiac parameters comprises:
   deploying a temporary pacing and sensing lead into electrical communication with the heart.

5. A method according to claim 1, wherein the step of measuring the temporal cardiac parameters comprises:
   deploying a chronic pacing and sensing lead into communication with the heart.

6. A method according to claim 1, wherein the step of measuring the temporal cardiac parameters comprises:
   deploying a subcutaneous cardiac sensing array into a position spaced from, but in electrical communication with, the heart.

7. A method according to claim 1, wherein the step of measuring the temporal cardiac parameters comprises:
   deploying at least one surface sensing electrode into communication with the heart.

8. A method according to claim 1, wherein the step of measuring the temporal cardiac parameters comprises one of:
   deploying a temporary pacing lead into communication with the heart.

9. A method according to claim 1, further comprising
   storing at least one of the following values in a memory structure: the sensed PWd value, the sensed PR interval value, the sensed or paced QRSd value, the HR value.

10. A method according to claim 1, wherein the parameters are measured via a vector between a defibrillation electrode and a portion of the housing of the device.

11. A method according to claim 1, further comprising:
    measuring at least one of PR and HR more frequently than at least one of PWd and QRSd; and
    calculating AVopt based upon the measured values.

12. A method according to claim 1, further comprising:
    calculating a sensed-AV (SAV) interval based upon the AVopt value.

13. A method according to claim 12, further comprising:
    measuring a current HR value, and wherein the calculated SAV interval is decremented in the event that the current HR value is increasing.

14. A method according to claim 13, wherein the SAV interval is decremented between about 0.25 milliseconds (ms) and about 3 ms for each additional beat per minute (bpm) the HR value increases.

15. A method according to claim 1, further comprising:
calculating a paced-AV (PAV) interval based upon the AVopt value.

16. A method according to claim 15, further comprising:
measuring a current HR value, and wherein the calculated SAV interval is decremented in the event that the current HR value is increasing.

17. A method according to claim 16, wherein the SAV interval is decremented between about 0.25 milliseconds (ms) and about 3 ms for each additional beat per minute (bpm) the HR value increases.

18. An apparatus for adjusting an operating atrio-ventricular (AV) interval in a cardiac pacing therapy delivery device, comprising:
means for measuring the following temporal cardiac parameters of a subject's heart: a P-wave duration (PWd) value, a sensed intrinsic atrioventrical (PR) interval, a sensed or paced QRS duration (QRSd) value, and a heart rate (HR) for at least one cardiac cycle;
means for calculating an optimized AV interval (AVopt) as a linear function of the sensed PWd value, the sensed PR interval value, the sensed or paced QRSd value, and the HR value; and
means for storing the calculated AV interval as an operating AV interval in a memory structure of a pacing therapy delivery device for diverse values of the measured parameters.

19. An apparatus according to claim 18, further comprising:
means for operating the device in a bi-ventricular pacing mode based at least in part upon the optimized AV interval.

20. A non-transitory computer medium for storing executable instructions operable under computer processor control to adjust an operating atrio-ventricular (AV) interval in a cardiac pacing therapy delivery device, comprising:
instructions:
instructions for measuring the following temporal cardiac parameters of a subject's heart: a P-wave duration (PWd) value, a sensed intrinsic atrioventrical (PR) interval, a sensed or paced QRS duration (QRSd) value, and a heart rate (HR) for at least one cardiac cycle;
instructions for calculating an optimized AV interval (AVopt) as a linear function of the sensed PWd value, the sensed PR interval value, the sensed or paced QRSd value, and the HR value; and
instructions for storing the calculated AV interval as an operating AV interval in a memory structure of a pacing therapy delivery device.

21. A non-transitory computer readable medium according to claim 20, further comprising:
instructions for operating the device in a bi-ventricular pacing mode based at least in part upon the optimized AV interval.

22. An apparatus for adjusting an operating atrio-ventricular (AV) interval in a pacing therapy delivery device, comprising:
at least a pair of electrodes adapted to sense a PQRST complex, and including a P-wave, a sensed intrinsic atrioventrical event (PR), a QRS complex, a heart rate (HR, based on successive R-waves);
a processor coupled to the at least a pair of electrodes and adapted to determine a P-wave duration (PWd) value beginning from a sensed atrial event, an intrinsic atrioventrical (PR) interval based upon, a sensed or paced QRS duration (QRSd) value, and a heart rate (HR) for at least one cardiac cycle;
means for calculating an optimized AV interval (AVopt) as a linear function of the sensed PWd value, the sensed PR interval value, the sensed or paced QRSd value, and the HR value; and
a memory structure adapted to receive the AVopt from the means for calculating as an operating AV interval in a pacing therapy delivery device for diverse values of the measured parameters.

* * * * *